United States Patent
Tsuchida et al.

(10) Patent No.: US 6,949,663 B2
(45) Date of Patent: Sep. 27, 2005

(54) CARBOXYLIC ACID-TYPE LIPID

(75) Inventors: Eishun Tsuchida, Tokyo (JP); Shinji Takeoka, Tokyo (JP); Keitaro Sou, Tokyo (JP); Haruki Ohkawa, Tokyo (JP); Katsura Mori, Kanagawa (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 10/416,275

(22) PCT Filed: Nov. 9, 2001

(86) PCT No.: PCT/JP01/09829

§ 371 (c)(1),
(2), (4) Date: Jul. 2, 2003

(87) PCT Pub. No.: WO02/38530

PCT Pub. Date: May 16, 2002

(65) Prior Publication Data

US 2004/0028638 A1 Feb. 12, 2004

(30) Foreign Application Priority Data

Nov. 10, 2000 (JP) ........................................ 2000-344458

(51) Int. Cl.[7] ............................................. C07C 233/00
(52) U.S. Cl. ............................. 554/58; 554/56; 554/57; 424/450; 564/123; 514/23
(58) Field of Search ........................ 424/450; 564/123; 514/23; 554/56, 57, 58

(56) References Cited

U.S. PATENT DOCUMENTS

| | | | |
|---|---|---|---|
| 4,873,322 A | | 10/1989 | Fechtig et al. |
| 5,206,027 A | * | 4/1993 | Kitaguchi .................. 424/450 |
| 5,370,877 A | * | 12/1994 | Rosenberg et al. ......... 424/450 |
| 6,096,801 A | | 8/2000 | Vincent et al. |

FOREIGN PATENT DOCUMENTS

| | | |
|---|---|---|
| EP | 99177 | 1/1984 |
| JP | 64-26777 | 1/1989 |
| JP | 8-277480 | 10/1996 |
| JP | 08277480 | * 10/1996 |
| WO | 96/24617 | 1/1996 |

* cited by examiner

*Primary Examiner*—Deborah D. Carr
(74) *Attorney, Agent, or Firm*—Wenderoth, Lind & Ponack, L.L.P.

(57) ABSTRACT

As a negatively charged lipid that can stably add negative charges to the surface of vesicles without side effects, the carboxyl acid-type lipid of the following general formula [1]:

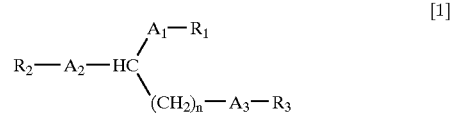

[1]

[wherein $R_1$, $R_2$ and $R_3$ represent substituents of which one is represented by the following general formula [X]:

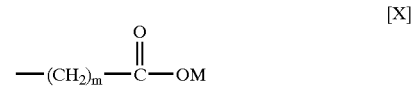

[X]

(wherein M is a hydrogen atom or monovalent cation, and m is an integer of 1 to 5 that represents the methylene chain length), and the other two are chained hydrocarbon groups; $A_1$, $A_2$ and $A_3$ are the same or different substituents selected from the group consisting of C(O)O, CONH or NHCO; and n is an integer of 1 to 3 that represents the methylene chain length) is provided.

8 Claims, No Drawings

CARBOXYLIC ACID-TYPE LIPID

This application is a U.S. National Stage of International Application No. PCT/JP01/09829 filed Nov. 9, 2001.

TECHNICAL FIELD

The invention of the present application relates to a carboxylic acid-type lipid that may be used as membrane lipids of vesicles. In particular, the invention of the present application relates to a negatively charged carboxylic acid-type lipid that may be used as the negatively charged component of molecular assemblies and molecular assembly membranes of vesicles, which enables the adjustment of surface charge density and surface hydration of the assembly, controlling of the number of layers of the multi-lamellar vesicle, and inhibition of inter-vesicle aggregation, depending on their structure and composition.

BACKGROUND ART

Vesicles encapsulating useful substances in the internal aqueous phase and their dispersions are an important technology in various fields such as pharmaceuticals, perfumes, cosmetics and food stuffs. Examples of widely used lipids that constitute the membrane of the vesicle include mixed lipids prepared by mixing negativ ly charged phospholipids such as diacylphosphatidyl glycerol, diacylphosphatidyl inositol, diacylphosphatidyl serine with diacylphosphatidyl choline or a mixture of diacylphosphatidyl choline and cholesterol in an arbitrary proportion.

However, diacylphosphatidyl glycerol, diacylphosphatidyl inositol, diacylphosphatidyl serine and diacylphosphatidyl ethanolamine that are currently introduced as negatively charged components in biologically applicable vesicle preparations are reported to induce aggregation of platelets in the body because they are physiologically active. It has been elucidated that administration of the vesicle preparations also causes severe side effects such as thrombocytopenia and dysfunction of white blood cells.

While long chain fatty acids have been used for a simplified method of introducing negative charges on the surface of the vesicle without using any negatively charged phospholipids, single chain fatty acids cannot be stably introduced into the molecular assembly. Instead, there is a problem that a part of the fatty acid leaks into the aqueous phase, or is extracted by lipoproteins and albumin in the blood.

Taking into account the above situations, the object of the invention of the present application is to solve the problems of the prior art, and to provide a negatively charged lipid that can stably add negative charges to the surface of a vesicle without any side effects.

DISCLOSURE OF INVENTION

In light of the above-mentioned circumstance, the inventors of the present invention achieved, as a result of intensive studies, the synthesis of carboxylic acid-type double chain lipids containing no phosphate groups using a compound that contains at least three functional groups as a spacer. The inventors also found that the carboxylic acid-type double chain lipid is stably fixed in phospholipid bilayer membranes, and prevents platelets from aggregating in the blood when the vesicles to which the carboxylic acid-type lipid is introduced are used as negatively charged components, thereby completing the invention of the present application.

Hence, as a means to solve the above-described problems, the invention of the present application firstly provides a carboxylic acid-type lipid represented by the following general formula [1]:

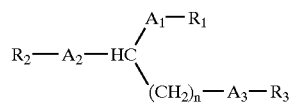

[wherein $R_1$, $R_2$ and $R_3$ represent substituents of which one is represented by the following general formula [X]:

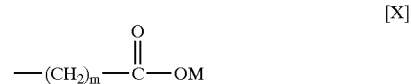

(wherein M is a hydrogen atom or monovalent cation, and m is an integer of 1 to 5 that repres nts th methylene chain length), and the other two are chained hydrocarbon groups; $A_1$, $A_2$ and $A_3$ are the same or different substituents selected from the group consisting of C(O)O, CONH or NHCO; and n is an integer of 1 to 3 that represents the methylene chain length].

Further, secondly, the invention of the present application provides a carboxylic acid-type lipid represented by the following general formula [2]:

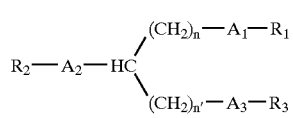

[wherein $R_1$, $R_2$ and $R_3$ represent substituents of which one is represented by the following general formula [X]:

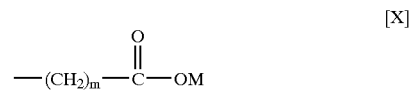

(wherein M is a hydrogen atom or monovalent cation, and m is an integer of 1 to 5 that represents the methylene chain length), and the other two are chained hydrocarbon groups; $A_1$, $A_2$ and $A_3$ are the same or different substituents selected from the group consisting of OC(O) and O; and n and n' are integers of 1 to 3 that represent the methylene chain length].

The invention of the present application thirdly provides a carboxylic acid-type lipid represented by the general formula [3]:

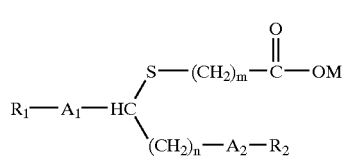

[wherein M is a hydrogen atom or monovalent cation; m is an integer of 1 to 5 that represents the methylene chain length; $R_1$ and $R_2$ are chained hydrocarbon groups; $A_1$ and $A_2$ are the same or different substituents selected from the group consisting of C(O)O and CONH; and n is an integer of 1 to 3 that represents the methylene chain length].

Fourthly, the invention of the present application provides a carboxylic acid-type lipid represented by the following general formula [4]:

$$R_4-O-C\begin{array}{c}CH_2-A_1-R_1\\A_2-R_2\\CH_2-A_3-R_3\end{array} \quad [4]$$

[wherein $R_1$, $R_2$ and $R_3$ represent substituents of which one is represented by the following general formula [X]:

$$-(CH_2)_m-\overset{O}{\underset{\|}{C}}-OM \quad [X]$$

(wherein M is a hydrogen atom or monovalent cation, and m is an integer of 1 to 5 that represents the methylene chain length), and the other two are chained hydrocarbon groups; $A_1$, $A_2$ and $A_3$ are the same or different substituents selected from the group consisting of C(O)O and CONH; and $R_4$ is selected from the group consisting of a hydrogen atom, methyl group and acetylene group].

The invention of the present application fifthly provides a carboxylic acid-type lipid represented by the following general formula [5]:

$$D\begin{array}{c}A_1-R_1\\A_2-R_2\\A_3-R_3\end{array} \quad [5]$$

[wherein $R_1$, $R_2$ and $R_3$ are substituents of which one is represented by the following general formula [X]:

$$-(CH_2)_m-\overset{O}{\underset{\|}{C}}-OM \quad [X]$$

(wherein M is a hydrogen atom or monovalent cation, and m is an integer of 1 to 5 that represents the methylene chain length), and the other two are chained hydrocarbon groups; $A_1$, $A_2$ and $A_3$ are the same or different substituents selected from the group consisting of OC(O). O, NH, CONH and NHCO; and D represents a saccharide].

Further, sixthly, the invention of the present application provides a carboxylic acid-type lipid represented by the following formula (6a] or [6b]:

[6a]

[6b]

[wherein either one of $R_1$ or $R_2$ is a hydrogen atom and the other is OR'''; either one of $R_3$ and $R_4$ is a hydrogen atom and the other is OR'''; R, R', R'', R''' and R'''' are substituents of which one is represented by the following general formula [Y]:

$$-A-(CH_2)_m-\overset{O}{\underset{\|}{C}}-OM \quad [Y]$$

(wherein M is a hydrogen atom or monovalent cation, A is $CH_2$ or CO, and m is an integer of 1 to 5 that represents the methylene chain length), at least two are chained hydrocarbon groups, and the others are hydrogen atoms; and n is an integer of 1 to 3 that represents the degree of polymerization].

Furthermore, the invention of the present application provides seventhly, a carboxylic acid-type lipid represented by the following general formula [7]:

$$(R_1)_p-(F)_q-R_2-(CH_2)_m-\overset{O}{\underset{\|}{C}}-OM \quad [7]$$

(wherein $R_1$ is an aliphatic hydrocarbon group, F is a monodendron constituting unit, $R_2$ is a linker, M is a hydrogen atom or monovalent cation, m is an integer of 1 to 5 that represents the methylene chain length, p is an integer of 2, and q is an integer of 1 to 4 that represents the number of repeating units in the dendron); and eigthly, the carboxylic acid-type lipid of the seventh invention, wherein the monodendron constituting unit is one or more amino acid, Ninthly, the invention of the present application provides a carboxylic acid-type lipid represented by the following general formula [8]

[8]

$$MO-\overset{O}{\underset{\|}{C}}-(CH_2)_m-\overset{O}{\underset{\|}{C}}-\underset{H}{N}-HC\begin{array}{c}\overset{O}{\underset{\|}{C}}-O-(CH_2)_nCH_3\\(CH_2)_2-\underset{\underset{O}{\|}}{C}-O-(CH_2)_{n'}CH_3\end{array}$$

(wherein M is a hydrogen atom or monovalent cation, m is an integer of 1 to 5 that represents the methylene chain length, and n and n' are integers of 13 to 21 that represent the chain lengths of methylene).

BEST MODE FOR CARRYING OUT THE INVENTION

The invention of present application provides the carboxylic acid-type lipids represented by the general formula [1] to [8].

In the carboxylic acid-type lipid represented by the general formula [1], the bonding site of $R_1$, $R_2$ and $R_3$ are preferably trifunctional amino acids. Specific examples of the amino acids include lysine, asparagine, glutamine, aspartic acid, glutamic acid, serine, threonine and tyrosine. Trifunctional amino acids having one reactive functional group and two equivalent functional groups (for example: aspartic acid and glutamic acid, which contain one terminal amino group and two terminal carboxylic groups; or lysine, glutamine and asparagine, which contain one terminal carboxylic group and two terminal amino groups) are preferable and glutamic acid and aspartic acid are particularly preferable. The amino acids may be homocysteine and glutathione.

For the carboxylic acid-type lipid represented by the general formula [2] of the invention of the present application, the bonding site of $R_1$, $R_2$ and $R_3$ is preferably glycerol. Further, for the carboxylic acid-type lipid represented by the general formula [3] of the invention of the present application, maleic acid is particularly preferable an the bonding site of $R_1$ and $R_2$. For the carboxylic acid-type lipid represented by the general formula [4], citric acid is preferably used as the bonding site of $R_1$, $R_2$ and $R_3$.

In the carboxylic acid-type lipid represented by the general formula [5] of the invention of the present application, the bonding site D is a saccharide. Further, in the carboxylic acid-type lipid represented by the general formula [6], the bonding sites of $R_1$ to $R_4$ are also a saccharide. Any saccharides may be used as long as they can be made hydrophobic by covalent bonds, and may be selected from various natural and synthetic saccharides. Examples of such saccharides are saccharides obtained by the α- or β-bonds of at least two monosaccharide units such as glucose, fructose, xylose, galactose, mannose and glucosamine, particularly maltose, cellobiose, lactose, xylobiose, isomaltose, gentiobiose, melibiose, boranteobiose, methinol, primeverose, bicyanose, nigerose, laminaribiose, turanose, kojibiose, sophorose, sucrose, trehalose, chitobiose, hyalurobiouronic acid, chondrosin, cellobiouronic acid, malto-oligosaccharide, laminario-oligosaccharide, cello-oligosaccharide, isomalto-oligosaccharide, gentio-oligosaccharide, nigero-oligosaccharide, lacto-oligosaccharide, meli-oligosaccharide and inulo-oligosaccharide; polysaccharide such as starch, pullulan, cellulose, muco-polysaccharide (hyaluronic acid, chondroitin, chondroitin sulfate, delmantan sulfate, ketaran sulfate, heparin), chitin and chitosan; and further, decomposition products of polysaccharides, cell and complex saccharides derived from bacteria. Among these, monosaccharides are preferable.

As the binding site (F) of the carboxylic acid-type lipid represented by the general formula [7] of the invention of the present application monodendron may be used. Such monodendron contains amino groups, carboxylic groups and hydroxyl groups at the branch terminus, and amino groups, carboxylic groups and hydroxyl groups as the core. Monodendrons with 1 to 5 branch generations are preferable. While F is preferably an amino acid such as lysine and glutamic acid wh n the monodendron is used as a biocompatible material, it is not restricted to them.

In the invention of the present application, among the substituents $R_1$ to $R_4$, one is represented by the above-described general formula [X] or [Y], and the rest are linear hydrocarbon groups. In the general formula [X] and [Y], M may be a hydrogen atom or a monovalent cation such as (although not limited to) $Na^+$, $K^+$, $Li^+$ and $NH_3^+$.

Furthermore, when the substituents of $R_1$ to $R_4$ are linear hydrocarbon groups, they may be hydrophobic groups introduced into the functional groups of amino acids, glycerol, maleic acid, citric acid, saccharides, cysteine, and monodendron by covalent bonding: straight or branched linear hydrocarbon groups with 1 to 30 carbons are preferable among them. Further, these groups may contain substituents such as carboxylic groups, hydroxyl groups and amino groups. When the linear hydrocarbon group contains unsaturated bonds, its number may preferably be 1 to 4.

Examples of the starting material for the above linear hydrocarbon group include saturated linear fatty acids containing carboxylic groups such as: caprylic acid, undecanoic acid, lauric acid, tridecanoic acid, myristic acid, pentadecanoic acid, palmitic acid, margarine acid, stearic acid, nonadecanoic acid, arachidic acid, behenic acid, lignoceric acid, cerotic acid, montanic acid and melissic acid; and unsaturated linear fatty acids such as obtusilic acid, linderic acid, thujic acid, fisetleic acid, palmitoleic acid petroceric acid, erucic acid, oleic acid, eladic acid, vaccenic acid, linolic acid, nervonic acid, linoelaidic acid, linolenic acid, γ-linolenic acid, bishomo-γ-linolenic acid and arachidonic acid. These may contain branched chains. Examples of branched fatty acid include iso-acids such as iso-lauric acid, iso-myristic acid, iso-palmitic acid, iso-stearic acid and iso-arachidic acid; and antiiso-acids such as 9-methyl undecanoic acid, 10-methyl dodecanoic acid, 11-methyl tridecanoic acid, 12-methyl tetradecanoic acid, 13-methyl pentadecanoic acid, 14-methyl hexadecanoic acid, 15-methyl heptadecanoic acid and 16-methyl octadecanoic acid. These acids may also be anhydrides and chlorides of these acids.

Further, examples of the starting materials of the linear hydrocarbon groups in the carboxylic acid-type lipid of the present invention include linear primary saturated alcohols containing hydroxyl groups such as decanol, lauryl alcohol, cetyl alcohol, stearyl alcohol, eicosanol, docosanol, tetracosanol, hexacosanol, octacosanol, nonacosanol and myristyl alcohol. Further examples include linear unsaturated alcohols, branched primary saturated alcohols, branched primary unsaturated alcohols, secondary saturated alcohols and secondary unsaturated alcohols examples of which are dodecenol, ficeterial alcohol, zomaryl alcohol, oleyl alcohol, gadoleil alcohol, 11-eicosenol, 11-docosenol, 13-docosenol, 15-tetracosenol, cathadonyl alcohol and linolenyl alcohol. Further examples include dialkyl glycerols comprising the primary saturated alcohols or primary unsaturated alcohols bonded to 1,3-position or 1,2-position of glycerin.

Further, examples of linear primary amines containing an amino group include dodecyl amine, tridecyl amine, tetradecyl amine, pentadecyl amine, hexadecyl amine, heptadecyl amine, octadecyl amine, docosyl amine and oleyl amine. These amines may contain branched chains.

In the carboxyl acid-type lipid of the present invention, the hydrophilic groups may be those that can be introduced into the functional groups of amino acids, glycerol, maleic acid, saccharides, cysteine and monodendron by covalent bond with or without the interposition of a spacer of an arbitrary length such as methylene groups or oxyethylene groups. The length of the methylene group, oxymethylene group, or the like may be approximately 0 to 1000, preferably, 1 to 5. Preferable examples of such hydrophilic groups include malonic acid, succinic acid, glutaric acid, adipic acid, pimelic acid and its anhydride, glycolic acid, 3-hydroxypropionic acid, 4-hydroxybutyric acid, 5-hydroxyvaleric acid 6-hydroxycaproic acid, bromoacetic acid, 3-bromopropionic acid, 4-bromobutyric acid, 5-bromovaleric acid and 6-bromocaproic acid (ethyleneglycol oligomers with both t rminus carboxylated, and ethyleneglycol oligomers carboxylated at one terminal).

While the bonding positions $A_1$, $A_2$ and $A_3$ to be used in the carboxylic acid-type lipid of the present invention may independently be selected from, an ester, ether, amide and imide, they are not restricted to these. $A_1$, $A_2$ and $A_3$ may be the same or different with each other.

Embodiments of the present invention will be described in further detail by means of examples with reference to the attached drawings. However, it is needless to say that the invention is not restricted to the examples below, and various aspects are possible with respect to the details.

EXAMPLE

Example 1

The First Invention

Glutamic acid (2.96 g, 20 mmol) p-toluene sulfonic acid (4.56 g, 24 mmol) and hexadecyl alcohol (10.65 g, 44 mmol) were dissolved in benzene (150 mL), and the solvent was refluxed at 100° C. for 14 hours while dehydrating the reaction system.

After removing the solvent under a reduced pressure, the reaction product was dissolved in chloroform, and the solution was washed three times with a saturated aqueous sodium hydrogencarbonate solution and three times with water, respectively.

The chloroform layer was dehydrated using sodium sulfate, filtrated, aft r which the solvent was removed under reduced pressure. The residue was dissolved in methanol (400 mL) at 60° C. and recrystallized at 4° C., after which the precipitate was filtrated and dried, where by a glutamic acid derivative [A] was obtained as a white solid (9.5 g, yield 80%). Compound [A] in which tetradecyl alcohol or octadecyl alcohol was bonded to glutamic acid was also synthesized by the same method

[A]

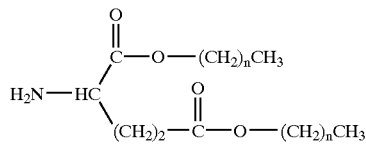

n = 13, 15, 17

The identification results are shown in Table 1.

TABLE 1

Thin layer chromatography (silica gel plate, chloroform/methanol 4/1 (volume/volume)): Rf: 0.79 (monospot).
Infrared absorption spectra (cm$^{-1}$): 3385[$V_{N-H}$ (NH$_2$)]; 1783[$V_{C=O}$(ester)].
$^1$H—NMR spectra[CDCl$_3$, 500MHz, δ (ppm)]: 0.88(t, 6H, —CH$_3$); 1.26(s, 52H, —CH$_2$—CH$_2$—); 1.62(m, 4H, CO—O—C—CH$_2$); 1.85, 2.08(m, 2H, glu β-CH$_2$); 2.46(m, 2H, glu γ-CH$_2$); 3.46(m, 1H, glu α-CH); 4.08, 4.12 (tt, 4H, —CO—O—CH$_2$—).

The resulting compound [A] (13.49 g, 2.5 mmol) was dissolved in a mixed solution of chloroform and tetrahydrofuran (mixing ratio 1:1 (volume/volume)), and the solution was stirred for 5 hours after adding succinic anhydride (0.38 g, 3.8 mmol). After removing the solvent under a reduced pressure, the reaction product was recrystallized from a mixed solvent of ethanol and acetone (mixing ratio 1:5 (volume/volume)) at 4° C., after which the precipitate was filtrated and dried; a negatively charged lipid [B] having a glutamic acid structure was obtained as a white solid (1.5 g, yield 86%).

[B]

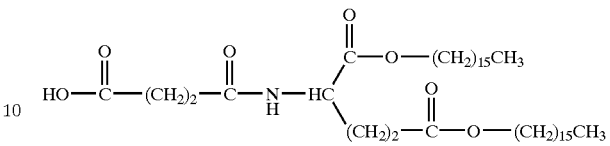

The identification results are shown in Table 2.

TABLE 2

Thin layer chromatography (silica gel plate, chloroform/methanol (4/1) (volume/volume)): Rf: 0.65 (monospot).
Infrared absorption spectra (cm$^{-1}$) 3314[$V_{N-H}$ (amide)]; 1734[$V_{C=O}$(ester)].
$^1$H—NMR spectra[CDCl$_3$, 500MHz, δ (ppm)]: 0.88(t, 6H, —CH$_3$); 1.26(s, 52H, —CH$_2$—CH$_2$—); 1.63(m, 4H, —CO—O—C—CH$_2$); 2.04, 2.21(m, 2H, glu β-CH$_2$); 2.40(m, 2H, —CH$_2$—CO—NH—); 2.58(m, 2H, glu γ-CH$_2$); 2.72(m, —CH$_2$—C—CO—NH—); 4.06, 4.14(tt, 4H, —CO—O—CH$_2$—); 4.60(m, 1H, glu α-CH); 6.55(m, 1H, —CO—NH—).
MS(FAB); calculated value for $C_{37}H_{73}O_4N$: 696.0; observed value: 696.5(M$^-$H)$^-$.

Example 2

The Second Invention

Glycerol (1.50 g, 32.6 mmol) and palmitic chloride (8.96 g, 32.6 mmol) were dissolved in dry chloroform, and the solution was stirred for 6 hours at room temperature under the presence of dimethylaminopyridine (3.98 g, 32.6 mmol). The reaction solution was washed with sodium chloride solution, saturated aqueous sodium hydrogencarbonate solution and saturated sodium chloride solution, after which the chloroform layer was recovered and concentrated under reduced pressure, followed by recrystallization from hexane. The crystal was filtrated, dissolved in chloroform, and further filtrated through a silica gel column (5×15 cm), whereby a glycerol derivative with palmitoyl groups at the 1- and 3-positions were obtained (5.56 g, yield 60%).

[C]

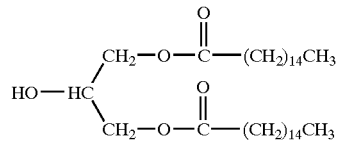

The identification results are shown in Table 3.

TABLE 3

Thin layer chromatography (silica gel plate, chloroform): Rf 0.40, (monospot).
Infrared absorption spectra (cm$^{-1}$): 3420[$V_{O-H}$ (hydroxyl group)]; 1748[$V_{C=O}$(ester)].
$^1$H—NMR spectra[CDCl$_3$, 500 MHz, δ (ppm)]: 0.88(t, 6H, —CH$_3$); 1.26(s, 56H, —CH$_2$—CH$_2$—); 1.63(t, 4H, —CO—O—C—CH$_2$); 3.1(m, 1H, glycerol CH); 3.40(m, 4H, glycerol CH$_2$).

The glycerol derivative [C] (4 g, 7.03 mmol) and adipic anhydride (1.03 g, 7.04 mmol) were dissolved in dry THF, and the solution was refluxed for 5 hours in the presence of a catalytic amount of DMAP (42 mg, 0.35 mmol). After removing the solvent under reduced pressure, the residue was dissolved in dichloromethane, and the solution was filtered to remove insoluble impurities followed by removing the solvent again under reduced pressure. The residue was dissolved in chloroform, and the solution was passed through a silica gel column to elute any unreacted compound [C]. After confirming the completion of elution, the solvent was substituted by ethyl acetate, whereby compound [D] having palmitoyl chains at the 1- and 3-positions, and a carboxylic group at the 2-position was obtained at a yield of 80%.

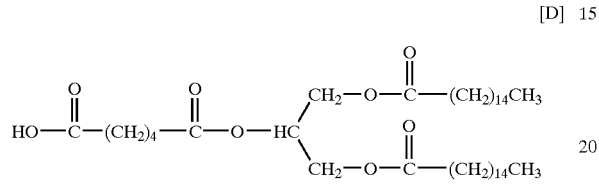

[D]

The identification results for the glycerol derivative [D] are shown in Table 4.

TABLE 4

Thin layer chromatography (silica gel plate, chloroform): Rf; 0.05 (monospot).
Infrared absorption spectra (cm$^{-1}$): 3321–2690[$V_{O-H}$ (carboxylic acid)]; 1748[$V_{C-O}$(ester)]; 1695[$V_{C-O}$ (carboxylic acid)].
$^1$H—NMR spectra[CDCl$_3$, 500MHz, δ (ppm)]; 0.88(t, 6H, —CM$_3$) 1.26(s, 56H, —CH$_2$—CH$_2$—); 1.63(t, 4H, —CO—O—C—CH$_2$); 2.66(m, 8H, —CH$_2$ adipic acid); 3.33(m, 1H, glycerol —CH); 3.40(m, 4H, -glycerol CH$_2$).

Example 3

The Third Invention

Maleic acid (2.32 g, 20 mmol), p-toluene sulfonic acid (4.56 g, 24 mmol) and hexadecyl alcohol (10.56 g, 44 mmol) were dissolved in benzene (150 mL), and the solvent was refluxed at 100° C. for 6 hours while removing water generated by the reaction. The reaction solution was washed three times with saturated aqueous sodium hydrogencarbonate solution and three times with water. After removing the solvent under reduced pressure, the product was recrystallized from methanol (400 mL) at 4° C., and the crystal was filtrated and dried, whereby the maleic acid derivative [E] with the alkyl groups esterified to the carboxyl groups was obtained as a white solid (8.46 g, yield 75%). Production of the desired compound was confirmed by the appearance of C=O stretch vibration (1740 cm$^{-1}$) attributed to the ester bond in the infrared absorption spectrum.

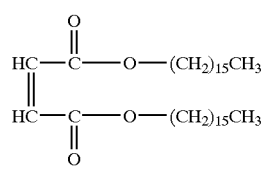

[E]

The resulting maleic acid derivative [E] (5.65 g, 10 mmol) and 3-mercaptopropionic acid (1.27 g, 12 mmol) were stirred at 25° C. for 24 hours. The product was recrystallized from methanol (200 mL) at 4° C., filtrated and dried, whereby a carboxylic acid double chain lipid [F] with a maleic acid structure was obtained as a white solid (4.68 g, yield 70%).

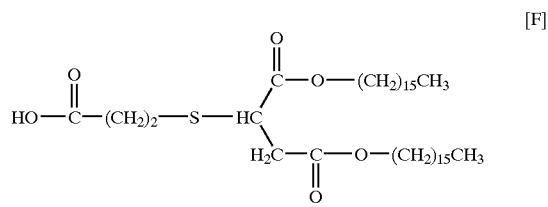

[F]

Example 4

The Fourth Invention

Citric acid (2.00 g, 10.5 mmol) was dissolved in 10 mL of acetic anhydride, and the solution was stirred at room temperature for 4 hours in the presence of $^1\!/_{20}$ equivalence of DMAP. A citric acid derivative with its hydroxyl groups protected by acetyl group was obtained by removing acetic anhydride under reduced pressure. Trace quantity of acetic acid odor disappeared by freeze drying from benzene. A peak attributing to an ester bond was confirmed in the IR spectrum at 1578 cm$^{-1}$ [$v_{C=O}$ (ester)]. The resulting hydroxyl group-protected citric acid was dissolved and dispersed in 100 mL of benzene, and p-toluene sulfonic acid (198 mg, 1.05 mmol) and hexadecyl alcohol (2.54 g, 208 mmol) were added to the solution. The mixture was reacted for 2 hours under refluxing while dehydrating, using a Dean-Stark apparatus. After confirming the disappearance of the starting alcohol from TLC, the solvent was removed under reduced pressure. The residue was dissolved in chloroform, and the solution was washed twice with 1M aqueous citric acid solution and twice with saturated sodium chloride solution. After drying the solution with anhydrous sodium sulfate, chloroform was removed under reduced pressure. The residue was dissolved in hot methanol and recrystallized, whereby compound [G] with palmitoyl chains at the 1- and 3-positions, and carboxylic and acetyl groups at the 2-position was obtained (5.26 g, 74%).

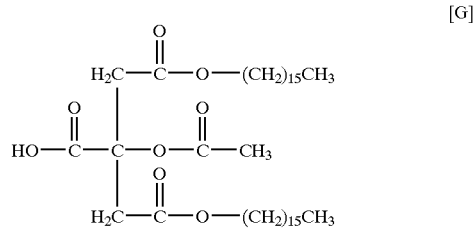

[G]

The identification results for the citric acid derivative [G] are shown in Table 5.

TABLE 5

Thin layer chromatography (silica gel plate, chloroform): Rf: 0.05 (monospot).
Infrared absorption spectra (cm$^{-1}$): 3321–2690[$V_{O-H}$ (carboxylic acid)]; 1748[$V_{C-O}$(ester)]; 1695[$V_{C-O}$ (carboxylic acid)].
MS (FAB): calculated value based on C$_{40}$H$_{74}$O$_6$: 683.0;

TABLE 5-continued observed value: 682.5 (M⁻H)⁻.
¹H—NMR spectra(CDCl₃, 500 MHz, δ (ppm)): 0.92(t, 6H,
—CH₃), 1.26(s, 56H, —CH₂—CH₂—); 1.63(t, 4H, —CO—O—
CH₂); 1.99(s, 3H, —COCH₃); 2.80(m, 4H, citric acid
—CH₂); 3.97(t, 4H, CO—O—CH₂).

Example 5

The Sixth Invention

Glucose (0.9 g, 5.0 mmol) was dissolved in dehydrated N,N'-dimethyl formamide (20 mL) and pyridine (2 mL), and stearic acid chloride (3.64 g, 12.0 mmol) was added dropwise to the solution. After stirring the reaction mixture for 3 hours while maintaining a temperature of 80° C., methanol (50 mL) was added to the reaction solution. The precipitate was recovered by filtration, washed with water and dried, whereby the saccharide derivative [H] with alkyl groups esterified to the hydroxyl groups was obtained as a white solid (2.67 g, yield 75%). Production of the desired compound was confirmed by the appearance of the C=O stretch vibration (1740 cm⁻¹) attributing to the ester bond in the infrared spectrum. The number of alkyl groups per glucose was calculated to be 2.1 from the nuclear magnetic resonance spectrum.

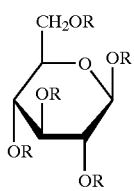

[H]

R: two are —C(=O)—(CH₂)₁₆CH₃
the rest are H

The resulting saccharide derivative [H] (2.14 g, 3.0 mmol) and succinic anhydride (0.36 g, 3.6 mmol) were dissolved in dehydrated N,N'-dimethyl formamide (20 mL), and the solution was stirred for 6 hours at 25° C. After removing the solvent under reduced pressure, the product was recrystallized from methanol (200 mL) at 4° C., filtrated and dried, and the carboxylic acid double chain lipid of [I] with a saccharide structure was obtained as a white solid (1.59 g, yield 70%). The number of uccinic acid bonded thereto per glucose was calculated to be 1.0 from the nuclear magnetic resonance spectrum.

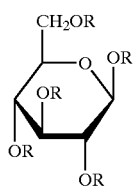

[I]

R: two are —C(=O)—(CH₂)₁₆CH₃

R: two are —C(=O)—(CH₂)₂C(=O)—OH the rest are H

Example 6

The Seventh Invention

L-glutamic acid (1.47 g, 10 mmol) and t-butoxycarbonyl anhydride (2.62 g, 12 mmol) were dissolve in a mixed solvent of dioxane (20 mL), water (10 mL) and 1N—NaOH (10 mL), and the solution was stirred at 25° C. for 6 hours. The solution was concentrated to 10 mL under reduced pressure, and 5% aqueous potassium hydrogen sulfate was added until the pH of the solution became 2.4, after which the solution was washed three times each with ethyl acetate, and water. After dehydrating the ethyl acetate layer with sodium sulfate, the solvent was removed under reduced pressure. The residue was recrystallized from hexane at 4° C., and the crystal was filtrated and dried; a monodendron derivative with t-butoxycarbonyl group (Boc group)-protected amino groups was obtained as a white solid (1.85 g yield 75%).

The identification results of the monodendron derivative are shown in Table 6.

TABLE 6

¹H—NMR spectra[CDCl₃, 500 MHz, δ (ppm)]: 1.40(s,
9H, —CH₃); 2.05(m, 2H, glu β-CH₂); 2.23(m, 2H,
glu γ-CH₂): 4.46(m, 1H, glu α-CH).

After dissolving the monodendron derivative (0.49 g, 2 mmol) and DCC (0.82 g, 4 mmol) in chloroform while stirring at 4° C. for 1 hour, the solution was added dropwise to a chloroform solution of compound [A] (2.98 g, 5 mmol) and triethylamine (0.20 g, 2 mmol). After stirring the reaction mixture solution at 25° C. for 6 hours, the solution was filtrated using a glass filter (G4), the filtrate was concentrated under reduced pressure, and the product was purified by re-precipitation with methanol. The precipitate was recovered by filtration, and was purified by silica gel column chromatography (solvent: chloroform/methanol=6/1 (volume/volume)) to obtain the monodendron derivative (1.40 g, yield 50%).

Production of the desired compound was confirmed by the appearance of an IR peak (1638 cm⁻¹) attributed to the amide bond.

The resulting monodendron derivative (1.40 g, 1 mmol) was dissolved in trifluoroacetic acid (TFA), and the solution was stirred for 1 hour to remove the protective group. The reaction solution was recrystallized from methanol at 4° C., and the crystal was filtrated and dried to obtain the monodendron derivative [J] (1.17 g, yield 90%).

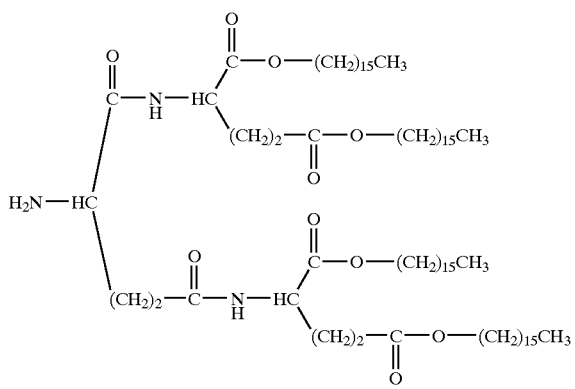

Production of the desired compound was confirmed from the disappearance of the methyl proton peaks ($\delta=1.44$) of the Boc group in $^1$H-NMR.

The monodendron derivative [J] (1.17 g, 0.9 mmol) was dissolved in a mixed solution of chloroform and tetrahydrofuran (mixing ratio 1:1 (volume/volume), and succinic anhydride (130 g, 1.35 mmol) was added, after which the solution was stirred for 5 hours. After removing the solvent under a reduced pressure, the residue was recrystallized from a mixed solution of ethanol and acetone (mixing ratio 1:5 (volume/volume)) at 4° C. The crystal was filtrated and dried, whereby a carboxylic acid tetra-chain lipid [K] with a monodendron structure (0.95 g, yield 75%) was obtained.

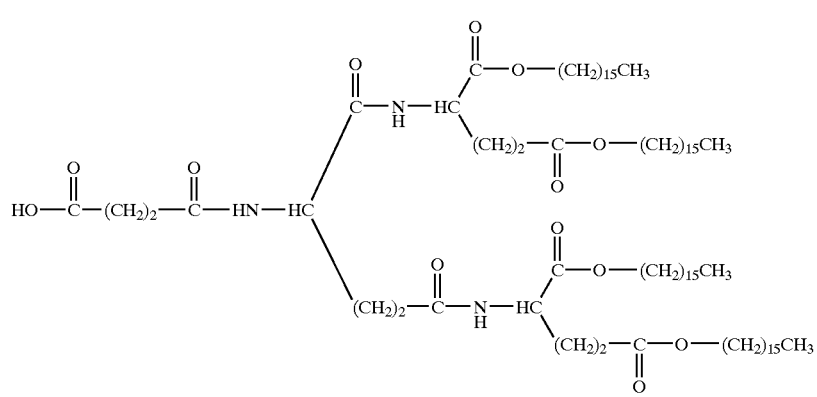

INDUSTRIAL APPLICABILITY

As described in detail above, the present invention provides a non-phospholipid carboxylic acid-type lipid. This lipid is effective for controlling the surface charge density and surface polarity of the phospholipid vesicle and for preventing vesicle aggregating and fusing in the same manner as phospholipids, such as diacylphosphatidyl glycerol (PG), diacylphosphatidyl inositol (PI), diacylphosphatidyl serine (PS) and diacylphosphatidyl ethanolamine (PE), which are generally used as membrane lipids of conventional vesicles do, and may further be used as the components of stable vesicle preparations for their excellent biocompatibility. Further, when administered in the body, particularly in the blood, this carboxyl acid-type lipid may also control the interactions among plasma proteins and blood cell components.

Moreover, a carboxyl acid-type lipid that may easily be synthesized is provided, and since the structure of the hydrophobic moiety can readily be changed, this carboxyl acid-type lipid may be applied as negatively charged amphiphilic molecules suitable for the use in various applications such as emulsifiers, stabilizers, dispersing agents, solubilizing agents, mixing agents wetting agents, permeating agents and viscosity modifiers in pharmaceuticals, food stuffs, cosmetics and dyes. Particularly, the lipid may be used as an artificial oxygen carrier if used as negatively charged lipids of vesicles containing hemoglobin.

What is claimed is:

1. A carboxylic acid-type lipid represented by the following general formula [2]:

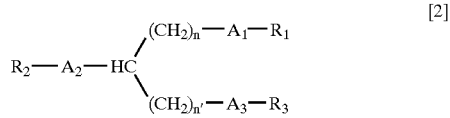

wherein $R_1$, $R_2$ and $R_3$ represent substituents of which one is represented by the following general formula [X]:

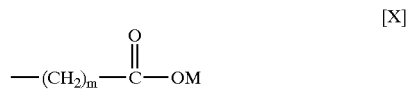

wherein M is a hydrogen atom or monovalent cation, and m is an integer of 1 to 5 that represents the methylene chain length, and the other two are chained hydrocarbon groups; $A_1$, $A_2$ and $A_3$ are the same or different substituents selected from the group consisting of OC(O) and O; and n and n' are integers that represent the methylene chain length and are 2 or 3.

2. A carboxylic acid-type lipid represented by the general formula [3]:

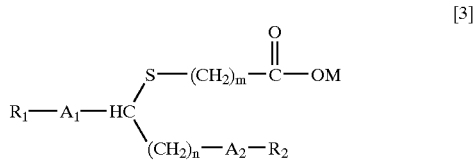

wherein M is a hydrogen atom or monovalent cation; m is an integer of 1 to 5 that represents the methylene chain length; $R_1$ and $R_2$ are chained hydrocarbon groups; $A_1$ and $A_2$ are the same or different substituents selected from the group consisting of C(O)O and CONH; and n represents the methylene chain length and is 2 or 3.

3. A carboxylic acid-type lipid represented by the following general formula [4]:

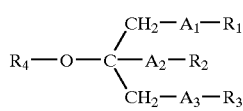

[4]

wherein $R_1$, $R_2$ and $R_3$ represent substituents of which one is represented by the following general formula [X]:

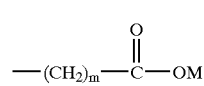

[X]

wherein M is a hydrogen atom or monovalent cation, and m is an integer of 1 to 5 that represents the methylene chain length, and the other two are chained hydrocarbon groups; $A_1$, $A_2$ and $A_3$ are the same or different substituents selected from the group consisting of C(O)O and CONH; and $R_4$ is selected from the group consisting of a hydrogen atom, methyl group and acetylene group.

4. A carboxylic acid-type lipid represented by the following general formula [5]:

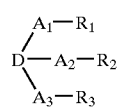

[5]

wherein $R_1$, $R_1$ and $R_3$ are substituents of which one is represented by the following general formula [X]:

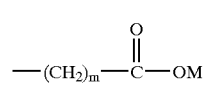

[X]

wherein M is a hydrogen atom or monovalent cation, and m is an integer of 1 to 5 that represents the methylene chain length, and the other two are chained hydrocarbon groups; $A_1$, $A_2$ and $A_3$ are the same or different substituents selected from the group consisting of OC(O), O, NH, CONH and NHCO; and D represents a saccharide.

5. A carboxylic acid-type lipid represented by the following formula [6a] or [6b]:

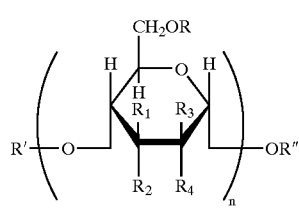

[6a]

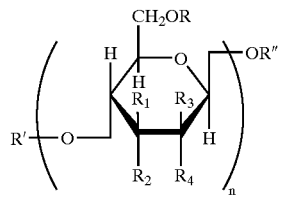

[6b]

wherein either one of $R_1$ or $R_2$ is a hydrogen atom and the other is OR'''; either one of $R_3$ and $R_4$ is a hydrogen atom and the other is OR''''; R, R', R'', R''' and R'''' are substituents of which one is represented by the following general formula [Y]:

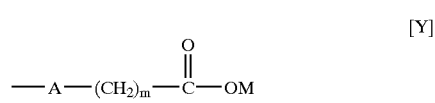

[Y]

wherein M is a hydrogen atom or monovalent cation, A is $CH_2$ or CO, and m is an integer of 1 to 5 that represents the methylene chain length, at least two are chained hydrocarbon groups, and the others are hydrogen atoms; and n is an integer of 1 to 3 that represents the degree of polymerization.

6. A carboxylic acid-type lipid represented by the following general formula [7]:

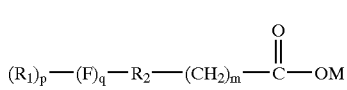

[7]

wherein $R_1$ is an aliphatic hydrocarbon group, F is a monodendron constituting unit, $R_2$ is a linker, M is a hydrogen atom or monovalent cation, m is an integer of 1 to 5 that represents the methylene chain length, p is an integer of 2, and q is an integer of 1 to 4 that represents the number of repeating units in the dendron.

7. The carboxylic acid-type lipid of claim 6, wherein the monodendron constituting unit is one or more amino acid.

8. A carboxylic acid-type lipid represented by the following general formula [8]:

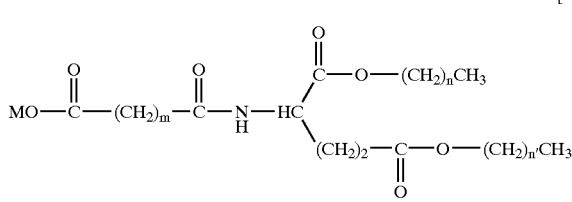

[8]

wherein M is a hydrogen atom or monovalent cation, m represents the methylene chain length and is 1, and n and n' are integers of 13 to 21 that represent the chain lengths of methylene.

\* \* \* \* \*